United States Patent [19]

Lee

[11] Patent Number: 4,644,089

[45] Date of Patent: Feb. 17, 1987

[54] CATALYTIC REFORMING OF HYDROCARBONS

[75] Inventor: Fu Ming Lee, Bartlesville, Okla.

[73] Assignee: Phillips Petroleum Company, Bartlesville, Okla.

[21] Appl. No.: 884,327

[22] Filed: Jul. 10, 1986

[51] Int. Cl.$^4$ .............................................. C07C 5/42
[52] U.S. Cl. .................................. 585/407; 585/379; 585/417; 585/430; 585/629; 585/661
[58] Field of Search ............... 585/379, 407, 417, 430, 585/629, 661

[56] References Cited

U.S. PATENT DOCUMENTS

| | | | |
|---|---|---|---|
| 2,189,815 | 2/1940 | Morrell et al. | 260/683 |
| 2,570,067 | 10/1951 | Myers | 260/683.3 |
| 2,726,195 | 12/1955 | Fleck et al. | 196/50 |
| 2,785,141 | 3/1957 | Fleck | 252/464 |
| 2,814,650 | 11/1957 | Clark | 260/668 |
| 2,941,016 | 6/1960 | Schmetterling et al. | 260/673.5 |
| 3,228,992 | 1/1966 | Myers | 260/666 |
| 3,320,331 | 5/1967 | Gaspar et al. | 260/683.3 |
| 3,374,281 | 3/1968 | Csicsery | 260/673 |
| 3,449,461 | 6/1969 | Jenkins | 260/673.5 |
| 3,585,248 | 6/1971 | Pasternak et al. | 260/669 |
| 3,585,249 | 6/1971 | Cohen et al. | 260/669 |
| 3,585,250 | 6/1971 | Pasternak et al. | 260/669 |
| 4,364,854 | 12/1982 | McDaniel et al. | 252/437 |
| 4,364,855 | 12/1982 | McDaniel et al. | 252/437 |
| 4,443,640 | 4/1984 | van de Meijden et al. | 585/418 |
| 4,607,129 | 8/1986 | Lee | 585/415 |

*Primary Examiner*—Curtis R. Davis
*Attorney, Agent, or Firm*—K. K. Brandes

[57] ABSTRACT

A process is provided for converting alkanes and cycloalkanes having up to 20 carbon atoms per molecule to a product comprising hydrogen gas and dehydrogenated and/or dehydrocyclized hydrocarbons, in the presence of a catalyst composition comprising vanadium oxide and aluminum phosphate. The preferred product components are aromatics such as ethylbenzene and xylenes. In one embodiment, a substantially deactivated catalyst composition is regenerated by contacting it with a free oxygen containing gas under suitable regeneration conditions.

20 Claims, No Drawings

CATALYTIC REFORMING OF HYDROCARBONS

BACKGROUND OF THE INVENTION

In one aspect, this invention relates to the catalytic dehydrogenation of alkanes to alkenes. In another aspect, this invention relates to the catalytic dehydrocyclization of alkanes to cycloalkenes and aromatic hydrocarbons. In still another aspect, this invention relates to the catalytic dehydrogenation of cycloalkanes to cycloalkenes and aromatic hydrocarbons. In a further aspect, this invention relates to a catalytic process for upgrading gasoline-type hydrocarbon mixtures to fuels having a higher octane rating.

Catalytic processes for the dehydrogenation and/or dehydrocyclization of alkanes and cycloalkanes are well known. Also processes for reforming of gasoline-type hydrocarbon fractions to fuels of higher octane rating are commercially practiced. However, there is an ever present need to develop new processes employing more effective catalysts for these important processes.

SUMMARY OF THE INVENTION

It is an object of this invention to provide a process for converting alkanes to alkenes and/or cycloalkenes and/or aromatic hydrocarbons by catalytic dehydrogenation and/or dehydrocyclization. It is another object of this invention to convert cycloalkanes to cycloalkenes and/or aromatic hydrocarbons by catalytic dehydrogenation. It is a further object of this invention to increase the octane number of gasoline-type hydrocarbons by reforming them in a dehydrogenation and/or dehydrocyclization reaction over a new reforming catalyst. It is a still further object to provide a process for regenerating a new reforming (dehydrogenation/dehydrocyclization) catalyst. Other objects and advantages will be apparent from the detailed description and the appended claims.

In accordance with this invention, a hydrocarbon feed stream comprising (preferably consisting essentially of) at least one hydrocarbon selected from the group consisting of alkanes containing from 2 to 20 carbon atoms per molecule and cycloalkanes containing from 5 to 20 carbon atoms per molecule is contacted with a catalyst composition comprising (preferably consisting essentially of) (a) at least one oxide of vanadium (preferably divanadium pentoxide) and (b) aluminum phosphate, in the substantial absence of free oxygen, steam and sulfur compounds and under such reaction conditions as to convert at least a portion of said hydrocarbon feed stream to a product comprising hydrogen gas and at least one hydrocarbon selected from the group consisting of alkenes containing from 2 to 20 carbon atoms, alkadienes containing from 4 to 20 carbon atoms per molecule, cycloalkenes containing from 5 to 20 carbon atoms per molecule, cycloalkadienes containing from 5 to 20 carbon atoms per molecule and aromatic hydrocarbons containing from 6 to 20 carbon atoms per molecule. Aromatic hydrocarbons are particularly preferred components of the product.

In a preferred embodiment, said hydrocarbon feed stream consists essentially of at least one alkane containing from 3 to 12 carbon atoms per molecule and said product comprises at least one aromatic hydrocarbon having from 6 to 12 carbon atoms. In another embodiment of this invention, a hydrocarbon feed mixture comprising alkanes containing from 5 to 12 carbon atoms per molecule and having a boiling range of about 50° F. to about 430° F. under standard pressure conditions (about 1 atmosphere) is contacted with a catalyst composition comprising (preferably consisting essentially of) (a) at least one oxide of vanadium (preferably $V_2O_5$) and (b) aluminum phosphate, under such conditions as to increase the octane number of the hydrocarbon mixture.

In still another embodiment, a catalyst composition comprising (preferably consisting essentially of) (a) at least one oxide of vanadium and (b) aluminum phosphate and having been contacted with a hydrocarbon feed in accordance with this invention is regenerated by contacting said catalyst composition with a free oxygen containing gas under such conditions as to enhance the dehydrogenation and/or dehydrocyclization activity of said catalyst composition. It is presently believed that a portion of divanadium pentoxide contained in the preferred catalyst composition is reduced to one or more oxides of vanadium having a lower valence state during said contacting with the hydrocarbon feed according to the process of this invention, and that said subsequent contacting of the catalyst with a free oxygen containing gas causes reoxidation of said lower valent vanadium oxides to divanadium pentoxide.

DETAILED DESCRIPTION OF THE INVENTION

The catalyst composition of this invention comprises (preferably consists essentially of) (a) vanadium oxide(s) and (b) aluminum phosphate (as support material). Preferably, catalyst component (a) is divanadium pentoxide, but lower oxides of vanadium (e.g., $VO_2$, $V_2O_3$, $VO$) can also be present in the catalyst composition.

It is within the scope of this invention, to have, in addition to vanadium oxide(s), small amounts of other metal oxides or sulfides such as $MoO_3$, $NiO$, $MoS_3$, $NiS$ and the like present in the catalyst composition. It is further within the scope of this invention, to have, in addition to silica, small amounts of other inorganic refractory oxides such as alumina, silica-aluminas, titania, zirconia, magnesia and the like present in the catalyst composition. However, it is preferred that the amounts of these other metal oxides or sulfides and inorganic refractory oxides are so small that they do not significantly affect the activity of the catalyst.

The catalyst composition of this invention can be prepared by any suitable method. Generally, a high surface area aluminum phosphate is impregnated with a solution of a suitable vanadium compound, and the thus impregnated aluminum phosphate is then heated (calcined), preferably in a free oxygen containing gas, so as to convert at least a substantial portion of said vanadium compound to divanadium pentoxide. Suitable calcining conditions are 900° to 1300° F. under 0 to 20 psig pressure.

Aluminum phosphate can be prepared by any method, generally by precipitation upon mixing of a solution containing $Al^{3+}$ ions and a second solution containing $H_3PO_4$ or $H_2PO_4^-$ or $HPO_4^{2-}$ or $PO_4^{3-}$ ions at a suitable pH, washing and calcining. Examples of such preparation methods are those described in U.S. Pat. No. 4,364,854 and 4,364,855, herein incorporated by reference. The preferred material support is aluminum phosphate having a surface area of at least 30 m²/g (as determined by the BET/$N_2$ method, ASTM D3037), more preferably from about 100 to about 400 m²/g. A presently preferred aluminum phosphate has an P:Al atomic ratio ranging from about 0.2:1 to about 1:1, more preferably from about 0.3:1 to about 0.8:1. Before calcining, the formula of the more preferred aluminum phosphate is $Al(PO_4)_a(OH)_b$, wherein a is a number ranging from about 0.3 to about 0.8 and $b=3-3a$. The specific P:Al atomic ratio in the aluminum phosphate support is not believed to be critical in this invention.

Suitable vanadium compounds that can be converted to vanadium oxide(s) upon heating are vanadium nitrates, vanadyl nitrates, ammonium vanadates, vanadium carboxylates, vanadium acetylacetonates, vanadium alcoholates and the like. The presently preferred impregnating solution is one containing vanadium oxobis(1-phenyl-1,3-butane dionate) as the solute and toluene as the solvent, or $VOSO_4.2H_2O$ as the solute and water as the solvent.

The vanadium content (expressed as weight-% vanadium metal) of the catalyst composition employed in the process of this invention can generally range from about 0.01 to about 25 weight-%, preferably from about 1 to about 5 weight-% V, based on the entire catalyst composition. The surface area (determined by the $BET/N_2$ method; ASTM D3037) of the finished (i.e., calcined) catalyst composition is in the range from about 30 to about 500 m$^2$/g, preferably from about 100 to about 400 m$^2$/g. The pore volume (determined by liquid nitrogen absorption) of the finished catalyst composition ranges from about 0.3 to about 4 cc/g, preferably from about 0.5 to about 2 cc/g.

The hydrocarbon feed to be treated in the process of this invention can contain at least one alkane having from 2 to 20 carbon atoms per molecule. Non-limiting examples of suitable alkanes are: ethane, propane, n-butane, isobutane, 2-methylbutane, n-pentane, 2-methylpentane, n-hexane, 3-methylhexane, 2,3-dimethylhexane, n-heptane, n-octane, n-decane, 3,4-dimethyldecane, 3-ethyldecane, n-dodecane, n-hexadecane, n-octadecane, 3-ethyloctadecane and the like. Preferred alkanes are those containing 3-12 carbon atoms per molecule, with n-octane being presently particularly preferred.

The hydrocarbon feed can also contain at least one cycloalkane having from 5 to 20 carbon atoms per molecule. Non-limiting examples of suitable cycloalkanes are cyclopentane, cyclohexane, cycloheptane, cyclooctane, cyclodecane, methylcyclopentane, methylcyclohexane 1,3-dimethylcyclohexane, 1,4-dimethylcyclohexane, ethylcyclohexane, methylcyclodecane, 1,3-dimethylcyclodecane, 1,3-dimethyl-5-propylcyclodecane and the like. Presently preferred cycloalkanes are cyclohexane, methylcyclohexane, 1,3-dimethyl-cyclohexane and ethylcyclohexane.

The hydrocarbon feed can also be a fraction of a petroleum crude oil, or a fraction of a catalytic cracker effluent, or a fraction of a shale oil, or a fraction of a product produced by extraction or liquefaction of coal, or of similar hydrocarbon-containing feed stocks. Preferably, a petroleum fraction boiling at atmospheric pressure in the range of about 50° F. to about 430° F. such as a gasoline or naphtha fraction is used as the feed. These fractions generally contain alkanes having from 5 to 12 carbon atoms per molecule as major components.

Free oxygen, steam and sulfur compounds (such as sulfur oxides, hydrogen sulfide, mercaptans and the like) must be substantially absent from the feed. Also, the presence of hydrogen gas in the feed at a concentration high enough to detrimentally affect the yield of aromatic hydrocarbons is not contemplated in the process of this invention. It is within the scope of this invention (but presently not preferred) to have relatively small amounts of olefins, cycloolefins and aromatics (i.e., the desired products) present in the feed.

Any apparatus which will afford an intimate contact of the hydrocarbon feed stream with the catalyst composition of this invention at an elevated temperature can be employed. The process is in no way limited to a particular apparatus. The process can be carried out in a batch process, e.g., in an autoclave which can be heated and pressured, and preferably contains internal agitating or circulating pumping means. The catalyst composition can be dispersed in the feed, or it can be used as a fixed bed through which the hydrocarbon feed flows. Or the process can be carried out as a continuous process, e.g., in a tubular reactor containing the catalyst composition as a fixed bed. The term "hydrocarbon feed stream" is used herein to both batch and continuous process.

The dehydrogenation/dehydrocyclization process of this invention can be carried out at any suitable temperature. Generally, the reaction temperature ranges from about 750° F. to about 1300° F., preferably from about 850° F. to about 1200° F., more preferably from about 900° F. to about 1100° F.

Any suitable reaction pressure can be utilized in the dehydrogenation process of this invention. The reaction pressure can generally range from approximately atmospheric (about 15 psia =0 psig) to as high as 500 psig. Preferably, the reaction pressure ranges from about 0 to about 100 psig, more preferably from about 0 psig to about 50 psig. The reaction is carried out in the substantial absence of added free oxygen, steam and sulfur compounds (as defined above) because of the detrimental effects of these compounds on the catalyst activity. Also, the amounts of hydrogen, if added with the feed (not preferred), should be so small that the yield of aromatics is not significantly affected.

Any suitable reaction time, i.e., the time of intimate contact of the hydrocarbon feed stream with the catalyst composition at suitable reaction conditions so as to remove hydrogen from said feed hydrocarbons, can be used in the process of this invention. The actual reaction time will greatly depend on such features as the selection of an effective, yet safe reaction temperature, the type of feed used, the type of catalyst bed employed and the particle size of the catalyst. Generally, the reaction time ranges generally from about 1 to about 20 seconds, preferably from about 4 to about 8 seconds. In a continuous process, the reaction time is generally expressed in terms of the weight hourly space velocity (weight of feed hydrocarbon/weight catalyst/hour), which can range from about 0.1 to about 10 g feed/g catalyst/hour, preferably from about 1 to about 2 g feed hydrocarbon/g catalyst/hour for the dehydrocyclization of alkanes, and preferably from about 1 to about 5 g feed hydrocarbon/g catalyst/hour for dehydrogenation of cycloalkanes.

The dehydrogenated products formed in the process of this invention are preferably separated from the reaction mixture by any separation means such as condensation, distillation, selective adsorption or absorption, extraction and the like, more preferably by fractional distillation. When the product is a mixture of compounds, further separation into individual compounds or fractions having a specific boiling range is preferably carried out. Unconverted feed hydrocarbons are preferably recycled to the reaction zone. Hydrogen gas which is formed during the process of this invention is preferably separated from other gaseous materials in any suitable conventional manner and can be used as fuel or as a reactant for chemical syntheses or chemical treating operations that require hydrogen (e.g., catalytic hydrotreating or hydrocracking of heavy oils).

The catalyst composition of this invention gradually loses its catalytic activity due to coking, and to a lesser extent due to partial reduction of divanadium pentoxide to oxides of vanadium having a lower valence state, during the process of this invention. In one embodiment of this invention, a substantially deactivated catalyst composition is regenerated by interrupting the flow of hydrocarbon feed and contacting the catalyst composition with a free oxygen containing gas (preferably air) at such regeneration conditions as will result in coke removal and the re-oxidization of lower vanadium oxides to divanadium pentoxide. The term "substantially deactivated catalyst composition" as used herein means a catalyst composition that has lost a sufficiently high portion of its initial activity that it no longer converts the feed hydrocarbon to the desired products at commercially acceptable yields. This regeneration process can be carried out in a separate reactor or it can be carried out in the same reactor as is used for the dehydrogenation/dehydrocyclization process, except that no hydrocarbon feed stream is passed through the reactor but a free oxygen containing gas, preferably air, is passed through the reactor. Typical regeneration conditions comprise a temperature ranging from about 700° F. to about 1300° F., using air as the free oxygen containing gas. Between contacts with hydrocarbon and with oxygen, the catalyst composition is preferably stripped by passing a stripping fluid such as nitrogen or other inert gases (e.g., He, Ar) through the catalyst composition.

In another embodiment of this invention, a swing-reactor operation with at least two parallel reactors containing catalyst beds was carried out for the regeneration of the catalyst. In this type of operation, the hydrocarbon feed flows through the first reactor under dehydrogenation/dehydrocyclization conditions. After the activity of the catalyst composition of this invention in the first reactor has decreased to an unacceptable level, a series of valves are actuated so that the feed is passed through at least one second reactor containing the catalyst composition of this invention under dehydrogenation/dehydrocyclization reaction conditions, while air is passed through the first reactor under the above described regeneration conditions. When the the catalyst composition in said second reactor has been substantially deactivated, appropriate valves are actuated so as to pass the hydrocarbon feed through the first reactor containing the regenerated catalyst composition and to pass air through said second reactor for catalyst regeneration. This cycle can be repeated many times. Stripping as described above is also preferably employed to prevent oxygen and hydrocarbon contact and to recover more hydrocarbon products.

The following examples are presented to further illustrate this invention without unduly limiting the scope of this invention.

EXAMPLE I

In this example the preparation of supported divanadium pentoxide catalysts is described.

Control Catalyst A ($V_2O_5$ on silica) was prepared as follows. A sample of 50 grams of silica (provided by Davison Chemical Division of W. R. Grace and Company, Baltimore, MD; surface area: 340 $m^2/g$; pore volume: 1.15 cc/g; volatile content at 1750° F.: 6.5%; bulk density: 25 $lb/ft^3$) was mixed at room temperature with a solution of 7.33 g of vanadium oxobis-(1-phenyl-1,3-butane-dionate) (provided by Eastman Kodak, Rochester, NY) in 200 mL of toluene. The mixture was slowly dried by heating in a ceramic drying dish. The dried, impregnated silica material was calcined in air for about 30 minutes at about 1200° F., and treated at this temperature with hydrogen (for reduction) and with air (for oxidation) in 10 alternating cycles each lasting about 5 minutes. The thus calcined and redox-treated $V_2O_5/SiO_2$ catalyst contained about 1.3 weight-% V, had a surface area (determined by BET/$N_2$; ASTM D3037) of 236 $m^2/g$ and a pore volume (determined by liquid nitrogen absorption) of 0.95 cc/g.

Control Catalyst B ($V_2O_5$ on alumina) was prepared by impregnating a sample of 25.2 g of alumina (surface area: 254 $m^2/g$; pore volume: 0.62 cc/g) with a solution of 2.5 g of vanadium oxobis-(1-phenyl-1,3-butane-dionate) in toluene. Drying, calcining and aging of the $V_2O_5/Al_2O_3$ catalyst were carried out essentially in accordance with the procedure described for Catalyst A. The thus calcined and redox-treated $V_2O_5/Al_2O_3$ catalyst contained about 1.2 weight-% V, had a BET/$N_2$ surface area of 153 $m^2/g$ and a pore volume (determined by liquid nitrogen absorption) of 0.56 cc/g.

Invention Catalyst C ($V_2O_5$ on aluminum phosphate) was prepared as follows. First, a concentrated solution containing aluminum and phosphate ions was prepared by melting a hydrate of aluminum nitrate, $Al(NO_3)_3.9-H_2O$, at 60°–80° C. and then dissolving in the melt an approximately stoichiometric amount of $NH_4HPO_4$. Concentrated aqueous ammonia was added to the solution so as to precipitate a hard gel of aluminum phosphate. The gel was aged in a dilute aqueous solution of ammonia, filtered washed with n-proponol, and dried at about 200° C.

50 grams of the thus formed aluminum phosphate having an P:Al atomic ratio of about 0.4:1 was mixed with an aqueous solution of 3.95 grams of $VOSO_4.2H_2O$ in 100 cc of warm, distilled water. The mixture was slowly dried on a hot plate and then under a heat lamp. The dried catalyst material was slowly heated in a quartz reactor to 1000° F. under nitrogen and then heated in air at about 1000° F. The cooled catalyst material was crushed and sieved using a 200 mesh screen. The portion having larger particle size than 200 mesh was employed as a catalyst in dehydrogenation/dehydrocyclizaiton runs.

The aluminum phosphate supported $V_2O_5$ catalyst contained 31.3 weight-% Al, 13.5 weight-% P and 1.5 weight-% V; and had a surface area (determined BET/$N_2$ method) of 214 $m^2/g$ and a pore volume (determined by liquid nitrogen absorption) of 1.23 cc/g.

EXAMPLE II

This example illustrates the conversion of n-octane to olefins and aromatics by dehydrogenation/dehydrocyclization over Catalysts A, B and C. The liquid feed (n-octane) was fed by means of a syringe pump through a 2 mm capillary tube into a heated vaporization chamber where the liquid was vaporized. The feed then passed through a heated catalyst bed. The feed flow rate generally ranged from about 2 to 4 WHSV (weight hourly space velocity; g feed/hour/g catalyst) and the weight ratio of catalyst to total feed used generally ranged from about 1.5 to 2. The reaction temperature was about 950° F. The liquid reaction products were collected in a trap cooled to 32° F., and non-condensed, gaseous products were collected in a gas receiver at room temperature. Liquid and gas products were analyzed by gas chromatography. Coke formation was determined from the weight gain of the catalyst after each run. Representative test results with catalysts A, B and C are summarized in Table I.

TABLE 1

|  | Run 1 | Run 2 | Run 3 |
|---|---|---|---|
| Catalyst[1] | A | B | C |
|  | (Control) | (Control) | (Invention) |
| WHSV | 4.0 | 2.9 | 2.9 |
| Catalyst/Feed Wt. Ratio | 1.7 | 1.9 | 1.9 |
| Temperature (°F.) | 950 | 950 | 950 |
| % Conversion | 29.8 | 39.7 | 26.2 |
| Wt % of Products: |  |  |  |
| Hydrogen | 1.1 | 0.23 | 0.80 |
| Methane | 0.57 | 2.42 | — |
| Ethane + Ethylene | 1.75 | 11.39 | 0.79 |
| Propane + Propylene | 1.53 | 6.63 | 0.90 |
| Butenes | 1.13 | 4.15 | 0.89 |
| Pentenes | 1.32 | 3.38 | 1.50 |
| Hexenes | 1.25 | 3.49 | 0.64 |
| Heptenes | 0.33 | 1.24 | 0.82 |
| Octenes | 2.87 | 0.22 | 1.08 |
| Nonenes | 0.61 | 0.12 | — |
| $C_4$–$C_8$ Alkanes | 0.50 | 1.11 | 0.94 |
| Benzene | 0.38 | — | 0.11 |
| Toluene | 0.61 | 0.25 | 0.68 |
| Ethylbenzene | 5.13 | 0.30 | 1.40 |
| p-Xylene | 0.41 | 0.11 | 0.81 |
| m-Xylene | 0.85 | 0.21 | 1.93 |
| o-Xylene | 6.87 | 0.41 | 2.44 |
| Coke | 1.87 | 1.20 | 1.97 |
| % Yield of Aromatics | 14.25 | 1.28 | 7.37 |
| % Selectivity to Aromatics[2] | 47.8 | 3.2 | 28.1 |

[1]All catalysts were oxidized in air at 1250° F. for 30 minutes before use.
[2](% Yield of Aromatics ÷ % Conversion) × 100.

Data in Table I show that the conversion of n-octane to aromatics was significantly higher over invention Catalyst C ($V_2O_5$/$AlPO_4$) than over control Catalyst B ($V_2O_5$/$Al_2O_3$). The main advantage of invention catalyst C versus control catalyst A ($V_2O_5$/$SiO_2$) in the tests of Example II was the greater yield of para-xylene and meta-xylene, which are valuable intermediates in the production of the corresponding phthalic acids and polyesters.

EXAMPLE III

This example illustrates the effect of hydrogen on catalysts A and C. Control catalyst A was treated with hydrogen for 20 minutes at about 1250° F., and invention catalyst C was treated with hydrogen for 20 minutes at about 1100° F. before n-octane was introduced with the reactor. The experimental setup was the same as the one described in Example II. Test results are summarized in Tables II and III.

TABLE II

|  | Run 1 | Run 4 |
|---|---|---|
| Catalyst | A | A |
|  | (Control) | (Control) |
| Catalyst Treated with $H_2$ | No | Yes |
| Feed | n-Octane | n-Octane |
| WHSV | 4.0 | 4.1 |
| Temperature (°F.) | 950 | 950 |
| Catalyst/Feed Wt. Ratio | 1.7 | 1.7 |
| % Conversion | 29.8 | 15.2 |
| Wt % of Products: |  |  |
| Hydrogen | 1.1 | 0.4 |
| Methane | 0.57 | 0.28 |
| Ethane + Ethylene | 1.75 | 1.19 |
| Propane + Propylene | 1.53 | 0.89 |
| Butenes | 1.13 | 0.94 |
| Pentenes | 1.32 | 0.78 |
| Hexenes | 1.25 | 0.64 |
| Heptenes | 0.33 | 0.34 |
| Octenes | 2.87 | 1.97 |
| Nonenes | 0.61 | 0.37 |
| $C_4$–$C_8$ Alkanes | 0.50 | 0.15 |
| Benzene | 0.38 | 0.11 |
| Toluene | 0.61 | 0.22 |
| Ethylbenzene | 5.13 | 1.18 |
| p-Xylene | 0.41 | 0.14 |
| m-Xylene | 0.85 | 0.26 |
| o-Xylene | 6.87 | 1.58 |
| Coke | 1.87 | 0.37 |
| % Yield of Aromatics | 14.25 | 3.49 |
| % Selectivity to Aromatics | 47.8 | 23.0 |

TABLE III

|  | Run 5 | Run 6 |
|---|---|---|
| Catalyst | C | C |
|  | (Invention) | (Invention) |
| Catalyst Treated with $H_2$ | No | Yes |
| Feed | n-Octane | n-Octane |
| WHSV |  |  |
| Temperature (°F.) | 1070 | 1035 |
| Catalyst/Feed Wt. Ratio | 3.8 | 3.8 |
| % Conversion | 43.4 | 38.2 |
| Wt % of Products: |  |  |
| Hydrogen | 2.17 | 1.88 |
| Methane | 2.72 | 1.36 |
| Ethane + Ethylene | 2.73 | 2.24 |
| Propane + Propylene | 4.32 | 1.71 |
| Butenes | 2.05 | 1.77 |
| Pentenes | 1.11 | 1.30 |
| Hexenes & Heptenes | 0.79 | 0.93 |
| Octenes | 1.04 | 0.99 |
| $C_4$–$C_8$ Alkanes | 0.71 | 0.66 |
| Benzene | 0.79 | 0.57 |
| Toluene | 1.62 | 1.36 |
| Ethylbenzene | 4.46 | 3.88 |
| p-Xylene | 1.48 | 1.38 |
| m-Xylene | 2.86 | 2.68 |
| o-Xylene | 6.13 | 5.34 |
| $C_9$ Aromatics | 0.17 | 0.15 |
| Coke | 6.06 | 3.08 |
| % Yield of Aromatics | 17.51 | 15.36 |
| % Selectivity to Aromatics | 40.3 | 40.2 |

Data in Table II show that the treatment of control catalyst A ($V_2O_5$/$SiO_2$) with $H_2$ resulted in a significant reduction (about 50%) of both octane conversion and selectivity to aromatics. Data in Table III show that, surprisingly, the treatment of invention catalyst C with $H_2$ resulted in only a minor reduction (about 10%) in octane conversion and in no detrimental effect on selectivity to aromatics.

EXAMPLE IV

This example illustrates the effects of oxygen, steam and hydrogen sulfide on the dehydrogenation/dehydrocyclization activity of invention catalyst C. Pertinent test results are summarized in Table IV and V.

TABLE IV

|  | Run 7 | Run 8 | Run 9 |
|---|---|---|---|
| Catalyst | C | C | C |
| Feed | n-Octane | n-Octane | n-Octane |
| Co—Feed | $N_2$ | Steam | Air |
| Rate of Co—Feed (cc/min.) | 80 | 80 | 80 |
| WHSV[1] | 2.5 | 2.5 | 2.5 |
| Temperature (°F.) | 1040 | 1040 | 1040 |
| Cat./Feed Wt-Ratio | 3.7 | 3.7 | 3.7 |

TABLE IV-continued

|  | Run 7 | Run 8 | Run 9 |
|---|---|---|---|
| % Conversion | 34.2 | 7.8 | 43.3 |
| Wt % of Products: |  |  |  |
| Hydrogen | 1.5 | 0.5 | 0.9 |
| $C_1$-$C_4$ Hydrocarbon | 6.0 | 7.5 | 22.0 |
| $C_5$-$C_8$ Olefins | 3.1 | 4.3 | 6.8 |
| Benzene | 0.1 | 0.1 | 0.1 |
| Toluene | 0.9 | 0.5 | 1.1 |
| Ethylbenzene | 3.0 | 0.4 | 2.3 |
| p-Xylene | 1.0 | 0.6 | 0.9 |
| m-Xylene | 2.0 | 1.0 | 1.7 |
| o-Xylene | 4.1 | 0.7 | 3.4 |
| Styrene | 0.2 | 0 | 0.2 |
| Coke | 4.8 | 2.1 | 3.5 |
| % Yield of Aromatics | 11.3 | 3.3 | 9.7 |
| % Selectivity to Aromatics | 33 | 19 | 22 |

[1]WHSV of n-Octane plus Co—Feed.

TABLE V

|  | Run 10 | Run 11 |
|---|---|---|
| Catalyst | C | C |
| Catalyst Sulfided with $H_2S$[1] | No | Yes |
| Feed | n-Octane | n-Octane |
| WHSV | 2.0 | 2.0 |
| Temperature (°F.) | 1040 | 1040 |
| Cat./Feed Wt-Ratio | 3.7 | 3.7 |
| % Conversion | 43.4 | 25.8 |
| Wt % of Products: |  |  |
| Hydrogen | 2.2 | 1.2 |
| $C_1$-$C_4$ Hydrocarbon | 12.2 | 4.4 |
| $C_5$-$C_8$ Olefins | 3.2 | 3.2 |
| Benzene | 0.8 | 0.3 |
| Toluene | 1.6 | 0.8 |
| Ethylbenzene | 4.5 | 2.2 |
| p-Xylene | 1.5 | 0.8 |
| m-Xylene | 2.9 | 1.6 |
| o-Xylene | 6.0 | 3.0 |
| Styrene | 0.2 | 0.2 |
| Coke | 6.1 | 2.2 |
| % Yield of Aromatics | 16.5 | 8.9 |
| % Selectivity to Aromatics | 40 | 34 |

[1]for 20 minutes at 1250° F.

Test data in Table IV show that the presence of steam during the dehydrogenation/dehydrocyclization had a detrimental effect on both conversion and selectivity to aromatics (Run 8 as compared with an inert gas as co-feed, Run 7). The presence of oxygen during the reaction (Run 9) caused a reduction in aromatics yield and selectivity to aromatics and a significant increase in the amount of light hydrocarbon ($C_1$-$C_4$), which are not desired in the dehydrogenation/dehydrocyclization reaction of this invention.

Test data in Table V show the detrimental effect of a sulfur compound on the performance of the catalyst of this invention: lower conversion and lower selectivity to aromatics.

EXAMPLE V

This example illustrates the reforming of a naptha fraction over the invention catalyst (1.5 weight-% V as $V_2O_5$ on aluminum phosphate) substantially in accordance with the experimental procedure described in Example II. The naptha feed had a RON-clear octane number (ASTM D2699) of 55.0. Test data are summarized in Table VI.

TABLE VI

|  | Run 12 | Run 13 |
|---|---|---|
| Catalyst | C | C |
| Feed | Naphtha | Naphtha |
| WHSV | 1.6 | 1.2 |
| Temperature (°F.) | 1070 | 1095 |
| Catalyst/Feed Wt. Ratio | 2.5 | 2.5 |
| Wt. % of Products: |  |  |
| Hydrogen | 1.9 | 2.5 |
| $C_1$-$C_4$ Hydrocarbon | 8.2 | 12.8 |
| $C_5$ + Hydrocarbons | 82.5 | 75.3 |
| Coke | 7.4 | 9.4 |
| RON of $C_5$ + Liquids | 78.5 | 87.0 |
| RON Increase | 23.5 | 32.0 |

Data in Table VI clearly show that $V_2O_5$ on aluminum phosphate as support can be successfully employed as a catalyst for increasing the octane number of gasoline and similar fuels.

Reasonable variations and modifications are possible within the scope of the disclosure and appended claims.

I claim:

1. A process comprising the step of contacting a hydrocarbon feed stream comprising at least one hydrocarbon selected from the group consisting of alkanes containing from 2 to 20 carbon atoms per molecule and cycloalkanes containing from 5 to 20 carbon atoms per molecule with a catalyst composition comprising (a) at least one oxide of vanadium and (b) aluminum phosphate, in the substantial absence of free oxygen, steam and sulfur compounds and under such reaction conditions as to convert at least a portion of said hydrocarbon feed stream to a product comprising hydrogen gas and at least one hydrocarbon selected from the group consisting of alkenes containing from 2 to 20 carbon atoms, alkadiene, containing from 4 to 20 carbon atoms, cycloalkenes containing from 5 to 20 carbon atoms, cycloalkadienes containing from 5 to 20 carbon atoms and aromatic hydrocarbons containing from 6 to 20 carbon atoms per molecule.

2. A process in accordance with claim 1, wherein said hydrocarbon feed stream contains at least one alkane having from 3 to 12 carbon atoms per molecule and said product contains at least one aromatic hydrocarbon having from 6 to 12 carbon atoms per molecule.

3. A process in accordance with claim 1, wherein the P:Al atomic ratio in said aluminum phosphate is in the range of from about 0.2:1 to about 1:1, the vanadium content of in said catalyst composition in in the range of from about 0.01 to about 25 weight-% V, based on the entire catalyst composition, and the surface area of said catalyst composition is in the range of from about 30 to about 500 m²/g.

4. A process in accordance with claim 3, wherein the vanadium content in said catalyst composition is in the range of from about 1 to about 5 weight-% V, based on the entire catalyst composition, and the surface area of said catalyst composition is in the range of from about 100 to about 400 m²g.

5. A process in accordance with claim 1, wherein said catalyst composition consists essentially of divanadium pentoxide and aluminum phosphate.

6. A process in accordance with claim 2, wherein said reaction conditions comprise a reaction temperature in the range of from about 750° F. to about 1300° F. and a reaction pressure in the range of from about 0 psig to about 500 psig.

7. A process in accordance with claim 1, wherein said reaction conditions comprise a reaction temperature in the range of from about 850° F. to about 1200° F., a reaction pressure in the range of from about 0 psig to about 100 psig and a reaction time in the range of from about 1 second to about 20 seconds.

8. A process in accordance with claim 1 comprising the additional step of separating said product from unreacted hydrocarbon feed.

9. A process in accordance with claim 1 comprising the additional step of separating hydrogen gas from said product.

10. A process in accordance with claim 1, wherein unconverted feed hydrocarbons are recycled to the reaction zone where said contacting is carried out.

11. A process in accordance with claim 1, wherein said at least hydrocarbon in said feed stream is n-octane.

12. A process in accordance with claim 1, wherein said at least one hydrocarbon in said feed stream comprises a mixture of alkanes containing from 5 to 12 carbon atoms per molecule and having a boiling range of about 50° F. to about 430° F. under standard pressure conditions.

13. A process in accordance with claim 12 wherein said product has a higher octane number than said hydrocarbon feed stream.

14. A process in accordance with claim 1 comprising the additional steps of
interrupting the flow of said hydrocarbon feed stream after said catalyst composition, which comprises divanadium pentoxide and aluminum phosphate, has been substantially deactivated due to coking and at least partial reduction of the divanadium pentoxide to oxides of vanadium having a lower valence state, and
contacting said substantially deactivated catalyst composition with a free oxygen containing gas under such regeneration conditions as will result in coke removal and in the re-oxidation of said oxides of vanadium having a lower valence state to divanadium pentoxide.

15. A process in accordance with claim 14 wherein said regeneration conditions comprise a temperature ranging from about 700° F. to about 1300° F., and the use of air as said free oxygen containing gas.

16. A process comprising the steps of
(A) adding a catalyst composition comprising (a) at least one oxide of vanadium and (b) aluminum phosphate to first reactor and second reactor, wherein said first reactor and said second reactor are in parallel;
(B) passing a hydrocarbon feed stream comprising at least one hydrocarbon selected from the group consisting of alkanes containing from 2 to 20 carbon atoms per molecule and cycloalkanes containing from 5 to 20 carbon atoms per molecule with said catalyst composition in said first reactor, in the substantial absence of free oxygen, steam and sulfur compounds and under such reaction conditions as to convert at least a portion of said hydrocarbon feed to a product comprising hydrogen gas and at least one hydrocarbon selected from the group consisting of alkenes containing from 2 to 20 carbon atoms, alkadienes containing from 4 to 20 carbon atoms, cycloalkenes containing from 5 to 20 carbon atoms, cycloalkadienes containing from 5 to 20 carbon atoms and aromatic hydrocarbons containing from 6 to 20 carbon atoms per molecule, until said catalyst composition is substantially deactivated;
(C) interrupting the flow of said hydrocarbon feed stream through said first reactor and passing said feed stream through said second reactor under such conditions as are employed in step (B);
(D) passing a free oxygen containing gas through the substantially deactivated catalyst composition in said first reactor under such regeneration conditions as will result in an increase of the activity of said catalyst composition;
(E) interrupting the flow of the hydrocarbon feed stream through said second reactor and passing said hydrocarbon feed stream through said first reactor under conditions as described in step (B); and
(F) passing a free oxygen containing gas through the substantially deactivated catalyst composition in said second reactor under such regeneration conditions as will result in an increase of the activity of said catalyst composition.

17. A process in accordance with claim 16, wherein a stripping fluid is passed through the substantially deactivated catalyst composition in said first reactor after step (C) and before step (D), and through the substantially deactivated catalyst composition in said second reactor after step (E) and before step (F).

18. A process in accordance with claim 17, wherein said stripping fluid is a gas selected from the group consisting of $N_2$, He and Ar.

19. A process in accordance with claim 16, wherein said regeneration conditions in steps (D) and (F) comprise a temperature in the range of from about 700° F. to about 1300° F.

20. A process in accordance with claim 16, wherein said catalyst composition consists essentially of divanadium pentoxide and aluminum phosphate.

* * * * *